United States Patent
Beger et al.

(10) Patent No.: US 9,095,395 B2
(45) Date of Patent: Aug. 4, 2015

(54) SURGICAL K-WIRE AND SURGICAL SCREW SYSTEM

(75) Inventors: Jens Beger, Tuttlingen (DE); Michael Pfeiffer, Obersaasheim (FR)

(73) Assignee: Aesculap AG, Tuttlingen (DE)

( * ) Notice: Subject to any disclaimer, the term of this patent is extended or adjusted under 35 U.S.C. 154(b) by 545 days.

(21) Appl. No.: 13/418,656

(22) Filed: Mar. 13, 2012

(65) Prior Publication Data

US 2012/0239052 A1 Sep. 20, 2012

(30) Foreign Application Priority Data

Mar. 14, 2011 (DE) .......... 10 2011 001 264

(51) Int. Cl.
*A61B 17/86* (2006.01)
*A61B 17/88* (2006.01)
*A61B 17/84* (2006.01)
*A61B 17/70* (2006.01)
*A61B 19/00* (2006.01)

(52) U.S. Cl.
CPC ........... *A61B 17/8897* (2013.01); *A61B 17/848* (2013.01); *A61B 17/8685* (2013.01); *A61B 17/7032* (2013.01); *A61B 17/84* (2013.01); *A61B 17/864* (2013.01); *A61B 17/8805* (2013.01); *A61B 17/8869* (2013.01); *A61B 2019/307* (2013.01)

(58) Field of Classification Search
CPC .... A61B 17/84; A61B 17/844; A61B 17/848; A61B 17/86; A61B 17/8635; A61B 17/8685
USPC ........... 606/96, 300, 301, 304, 313, 318, 328, 606/329
See application file for complete search history.

(56) References Cited

U.S. PATENT DOCUMENTS

| | | | | |
|---|---|---|---|---|
| 2,381,050 A | * | 8/1945 | Hardinge | ........................ 606/65 |
| 3,708,883 A | * | 1/1973 | Flander | ........................ 433/174 |
| 4,013,071 A | * | 3/1977 | Rosenberg | .................... 606/306 |
| 5,098,435 A | * | 3/1992 | Stednitz et al. | ............... 606/916 |
| 5,209,753 A | * | 5/1993 | Biedermann et al. | ......... 606/304 |
| 5,380,334 A | * | 1/1995 | Torrie et al. | .................... 606/104 |
| 5,720,753 A | * | 2/1998 | Sander et al. | .................. 606/104 |
| 6,214,012 B1 | | 4/2001 | Karpman et al. | |
| 6,755,835 B2 | | 6/2004 | Schultheiss et al. | |
| 6,997,930 B1 | | 2/2006 | Jäggi et al. | |
| 7,367,874 B2 | | 5/2008 | Schleicher | |
| 2002/0123752 A1 | | 9/2002 | Schultheiss et al. | |
| 2005/0287936 A1 | | 12/2005 | Schleicher | |
| 2006/0085008 A1 | | 4/2006 | Jäggi et al. | |
| 2009/0287218 A1 | | 11/2009 | Beger et al. | |
| 2010/0004692 A1 | | 1/2010 | Biedermann et al. | |

(Continued)

FOREIGN PATENT DOCUMENTS

| | | |
|---|---|---|
| CA | 2 405 230 | 10/2002 |
| DE | 203 03 657 | 8/2003 |

(Continued)

*Primary Examiner* — Nicholas Woodall
(74) *Attorney, Agent, or Firm* — Lipsitz & McAllister, LLC

(57) ABSTRACT

The present invention relates to a surgical K-wire for guiding a bone screw comprising a longitudinal channel, which said K-wire comprises a proximal and a distal end, wherein a closure element for closing-off the distal end outlet opening of the longitudinal channel of the bone screw is arranged or formed at the distal end.

Figure 1:
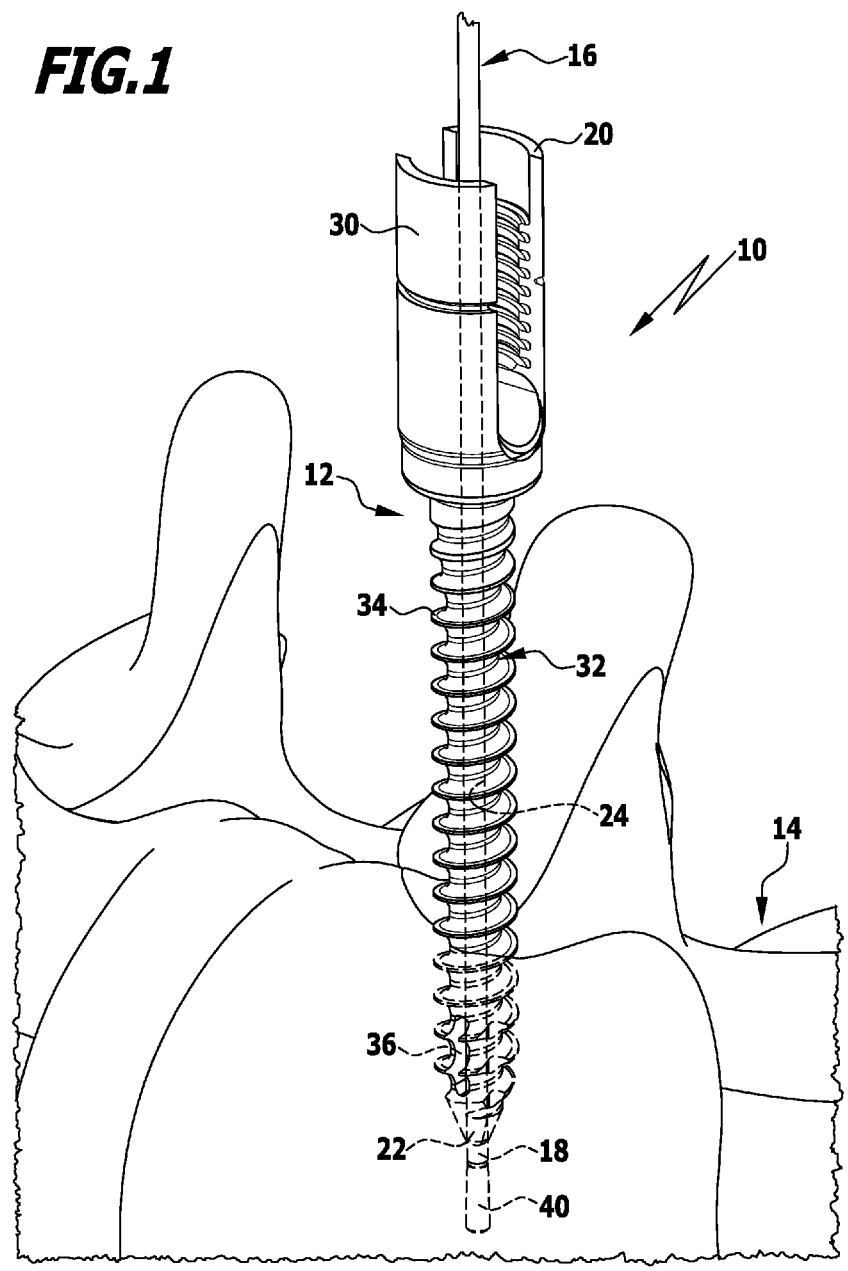

Furthermore, an improved surgical screw system is proposed comprising a bone screw and such a surgical K-wire.

18 Claims, 11 Drawing Sheets

(56) References Cited

U.S. PATENT DOCUMENTS

2010/0298892 A1* 11/2010 Biyani et al. .......... 606/318
2010/0331893 A1   12/2010 Geist et al.

FOREIGN PATENT DOCUMENTS

| | | |
|---|---|---|
| DE | 20 2008 006 870 | 9/2008 |
| EP | 0 434 604 | 6/1991 |
| EP | 1 294 322 | 2/2005 |
| EP | 1 204 382 | 9/2006 |
| EP | 1 210 019 | 7/2009 |
| JP | 2003159258 | 6/2003 |
| WO | WO 2009/010247 | 1/2009 |
| WO | WO 2010/127462 | 11/2010 |

* cited by examiner

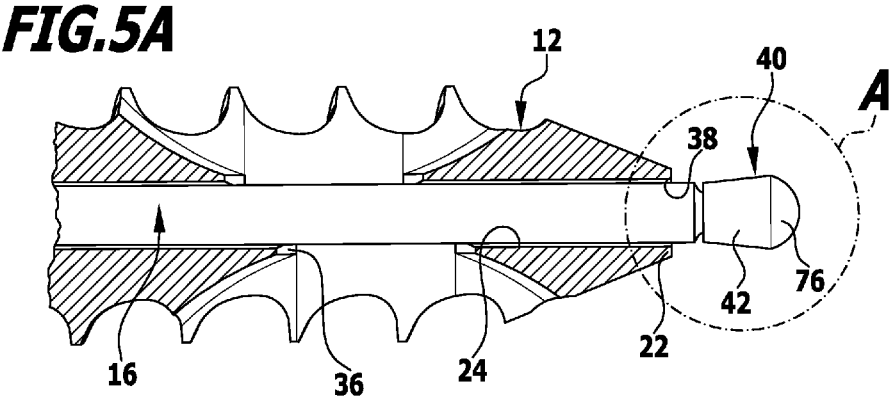
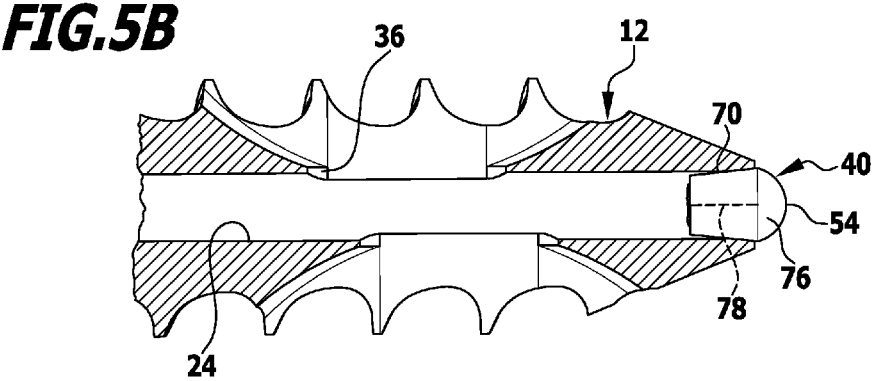
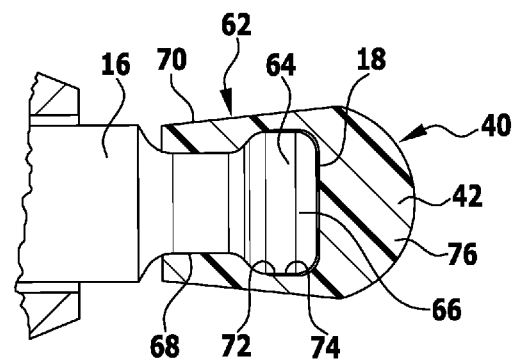

SURGICAL K-WIRE AND SURGICAL SCREW SYSTEM

CROSS-REFERENCE TO RELATED APPLICATIONS

The present disclosure relates to the subject matter disclosed in German patent application number 10 2011 001 264.8, filed Mar. 14, 2011, which is incorporated by reference herein in its entirety and for all purposes.

FIELD OF THE INVENTION

The present invention relates to surgical K-wires for guiding a bone screw generally, and more specifically to a surgical K-wire for guiding a bone screw comprising a longitudinal channel, which said K-wire has a proximal end and a distal end.

Furthermore, the present invention relates to surgical screw systems generally, and more specifically to a surgical screw system comprising a bone screw having a longitudinal channel extending from a proximal end to a distal end and a surgical K-wire for guiding the bone screw, which said K-wire has a proximal and a distal end.

BACKGROUND OF THE INVENTION

For the purposes of improving the stability thereof when anchoring bone screws, in the case of bone screws in the form of pedicle screws for example, they can be additionally fixed in the bone with the aid of bone cement. In principle thereby, bone cement can be injected into a pre-prepared hole in the bone. Thereafter, the screw is then screwed into the cement filling forming in the hole.

It is advantageous however to use a hollow screw which has a longitudinal channel extending from its proximal end to its distal end. After the screw has been implanted in the bone, the cement is injected through the longitudinal channel in the screw only after the implantation process. Screws are known which have lateral cement outlet openings that are connected to the longitudinal channel in fluid-conveying manner. As an option, the distal end of the screw could also be closed. The employment of screws of this type has the particular advantage that the cement can be injected in a controlled manner, and a uniform coating of cement can be formed around the screw commencing from the cement outlet openings.

From experience, cement does not normally emerge from the tip even in the case where the bone screw is open at the distal end if suitable lateral cement outlet openings have been provided. The reason for this is that the flow resistance for the bone cement is higher at the tip in dependence on the configuration of the lateral cement outlet openings. Nevertheless, there is a danger that the lateral cement outlet openings may become clogged by bone material when driving the screw into the bone. In practice, this cannot really be avoided so that one cannot completely eliminate a certain danger of cement emerging from the distal end. It can be particularly critical for example, if an osteoporosis screw being inserted into a vertebral body breaks through the contralateral bone of the vertebral body and the injected cement then, in the most unfavourable case, emerges ventrally of the vertebral body. In the course of biomechanical investigations, it could be established that hollow screws not using a K-wire become partially clogged and as a result the process of injecting cement is very difficult in certain circumstances.

Consequently, it would be desirable to provide a surgical K-wire and also a surgical screw system for minimizing emergence of bone cement at the distal end in the case of a completely channeled-out bone screw being guided by the K-wire.

SUMMARY OF THE INVENTION

In a first aspect of the invention a surgical K-wire for guiding a bone screw comprises a longitudinal channel. Said K-wire comprises a proximal and a distal end, wherein a closure element for closing-off the distal end outlet opening of the longitudinal channel of the bone screw is arranged or formed at the distal end.

In a second aspect of the invention a surgical screw system comprises a bone screw incorporating a longitudinal channel extending from a proximal end up to a distal end and a surgical K-wire for guiding the bone screw. Said K-wire comprises a proximal and a distal end, wherein a closure element for closing-off a distal end outlet opening of the longitudinal channel of the bone screw is arranged or formed at the distal end.

BRIEF DESCRIPTION OF THE DRAWING FIGURES

Figure 2A:
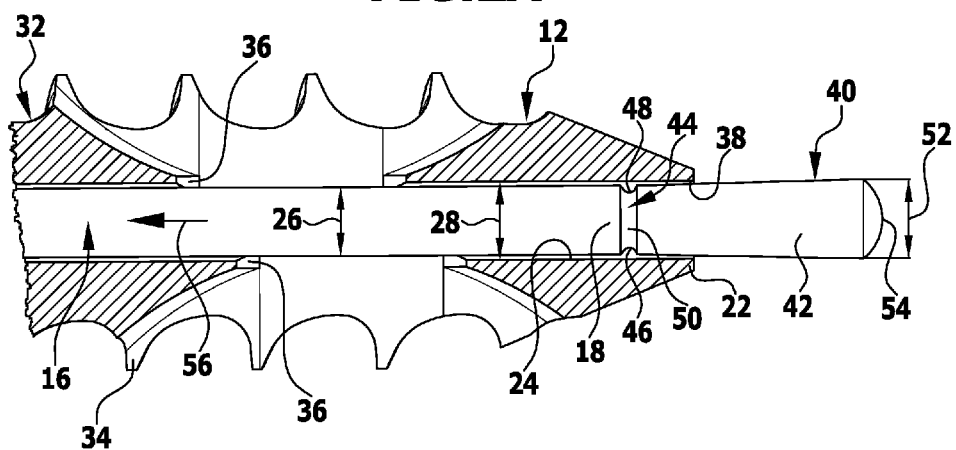
Figure 2B:
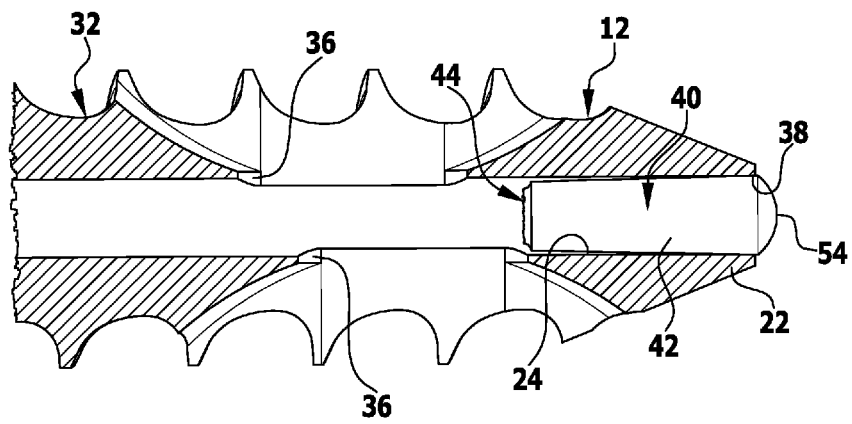
Figure 3A:
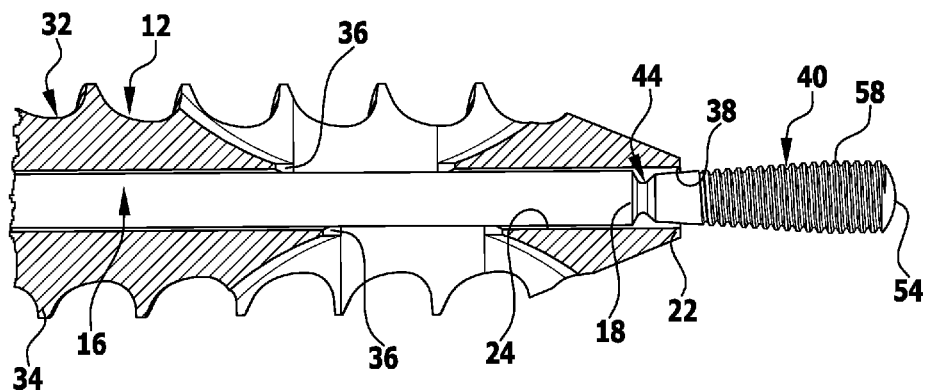
Figure 3B:
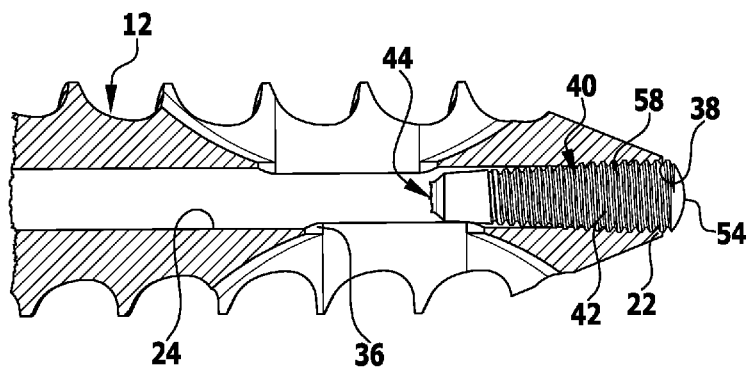
Figure 4A:
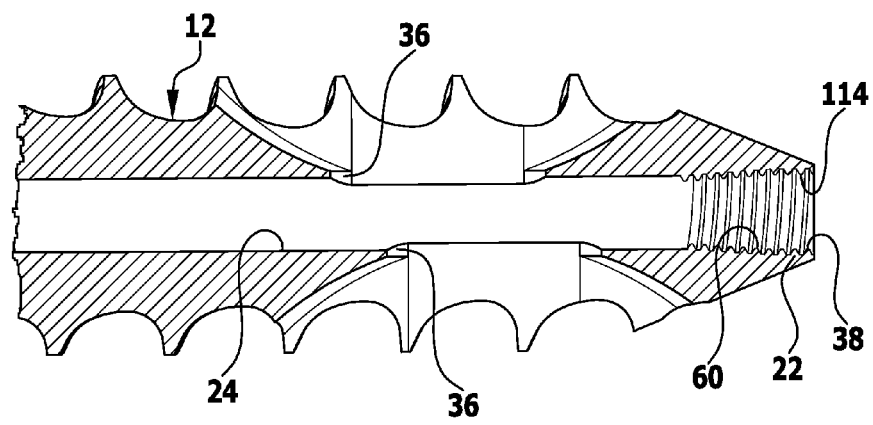
Figure 4B:
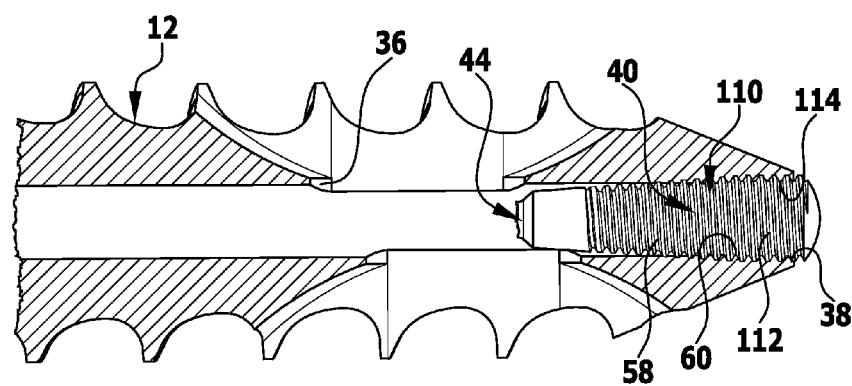
Figure 6A:
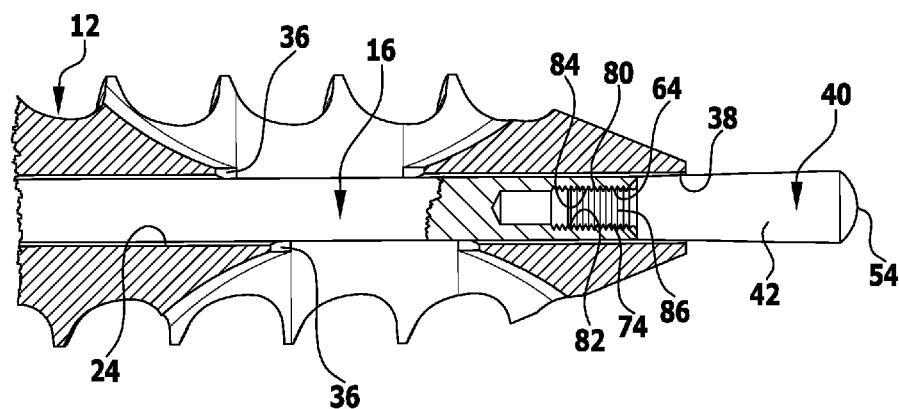
Figure 6B:
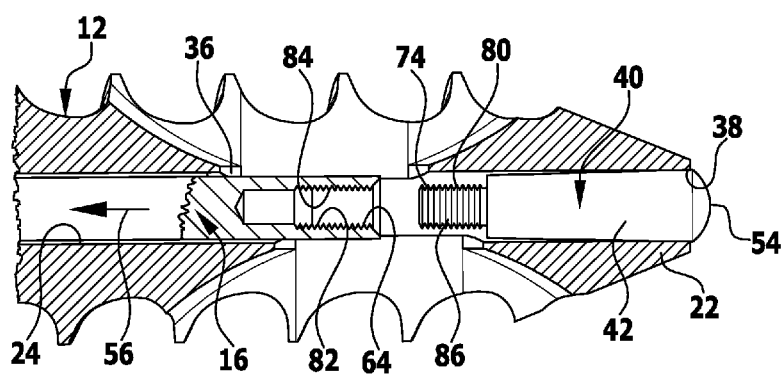
Figure 7A:
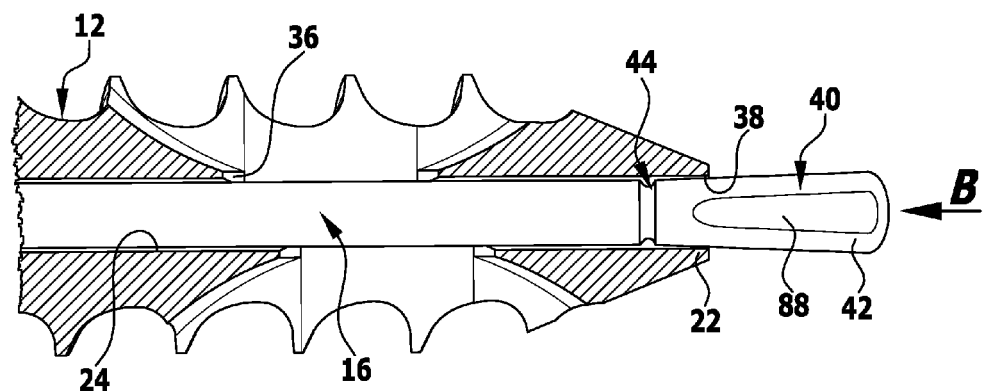
Figure 7B:
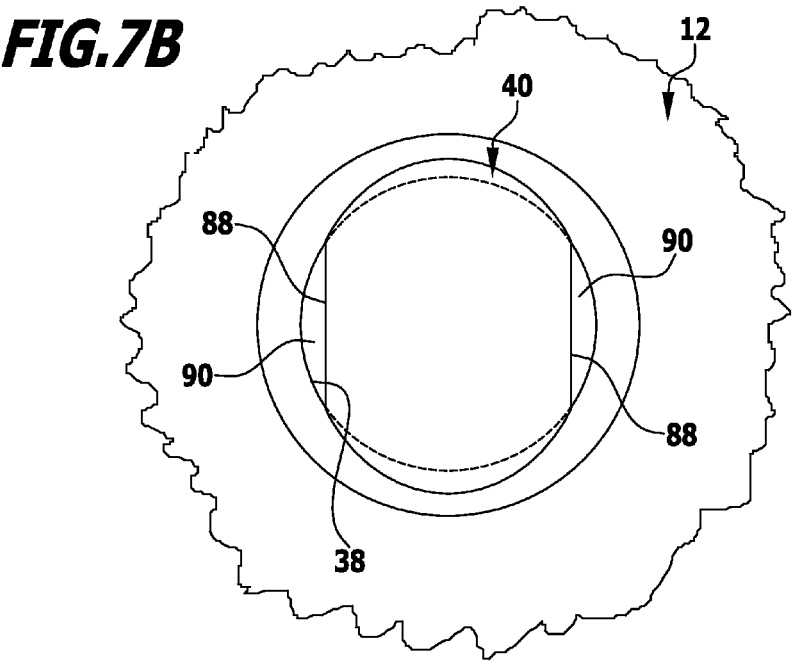
Figure 8A:
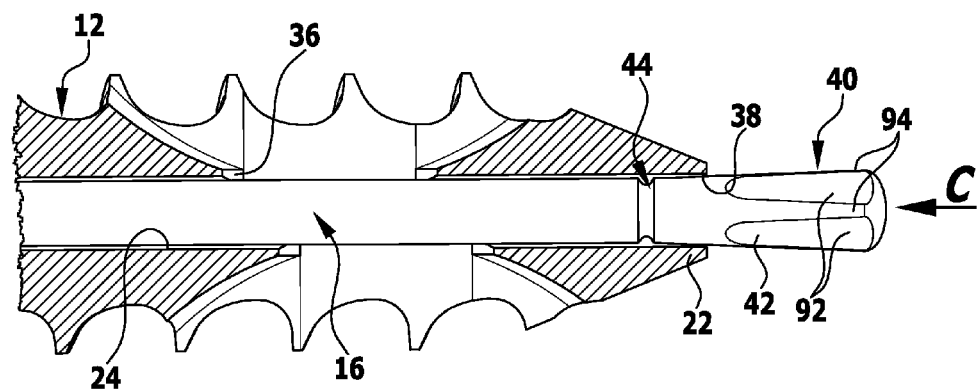
Figure 8B:
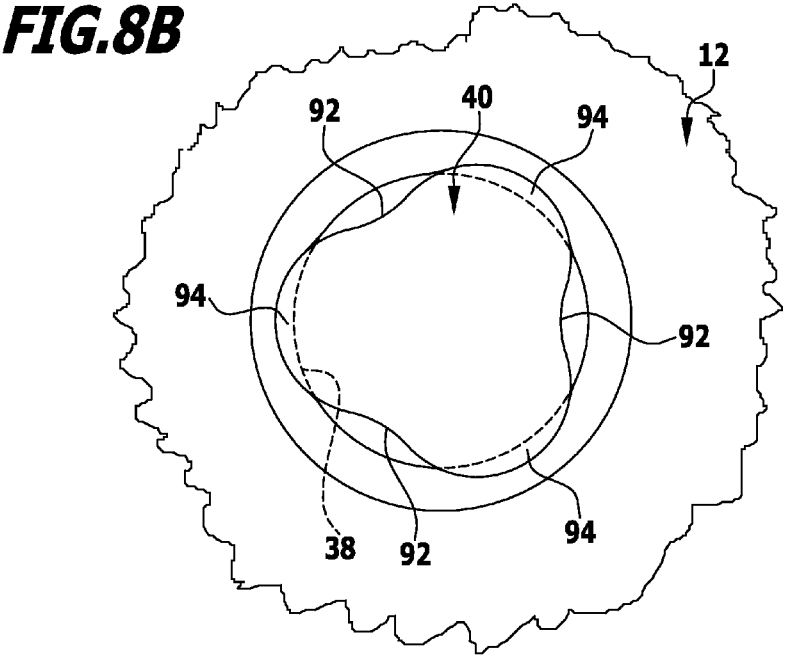
Figure 9:
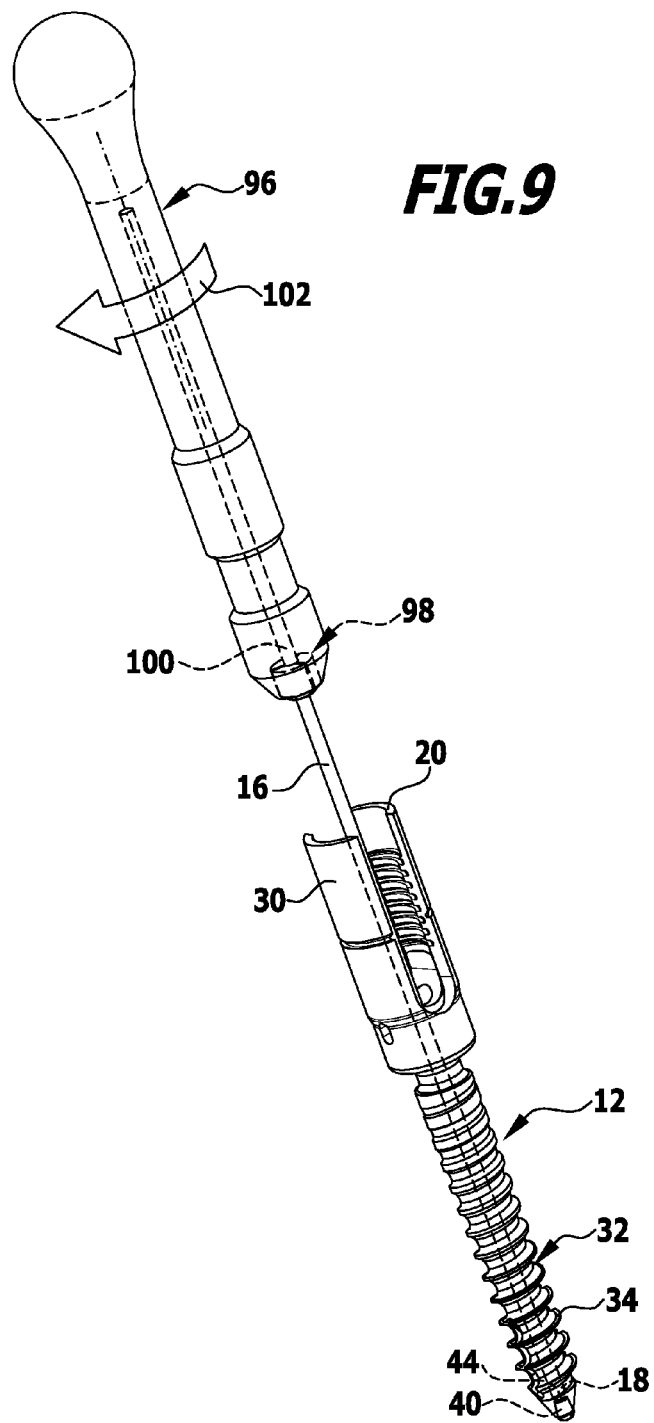
Figure 10A:
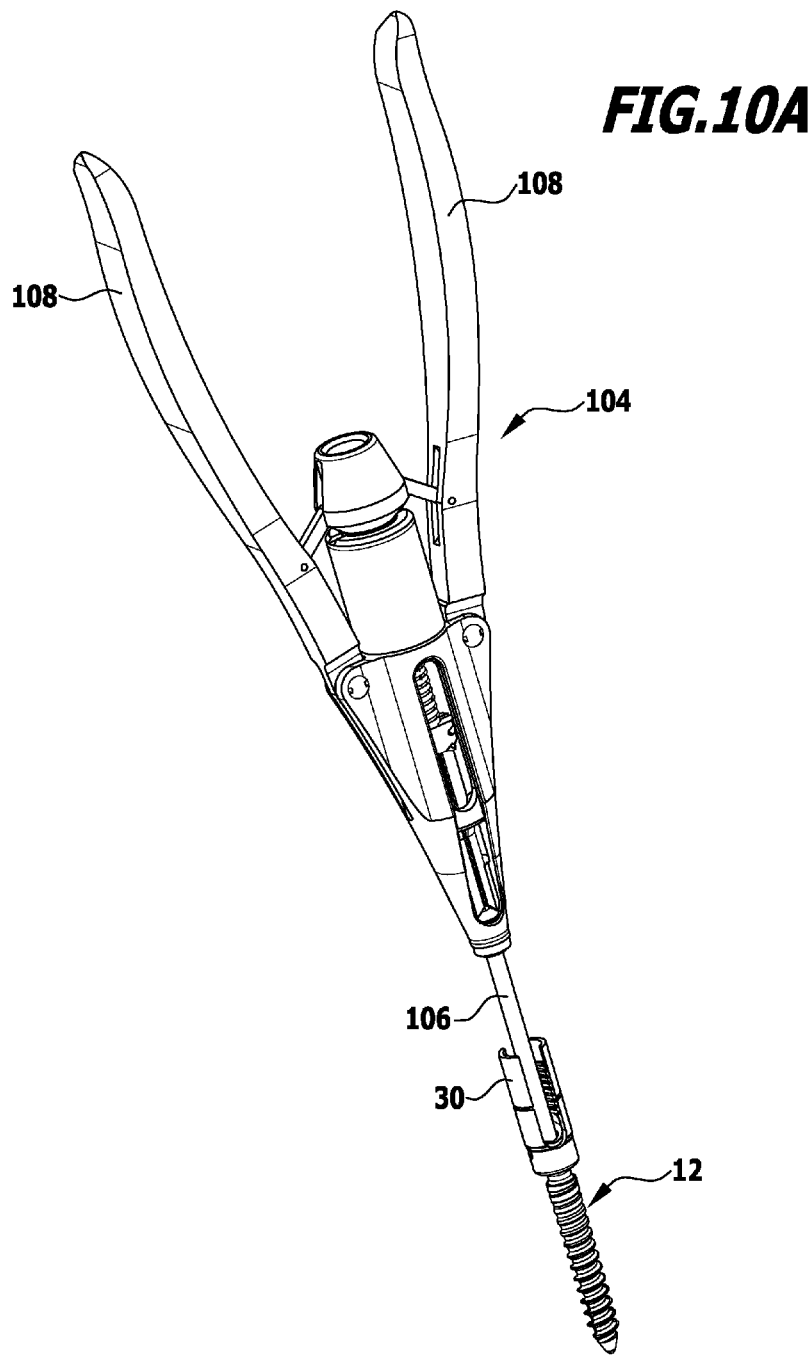
Figure 10B:
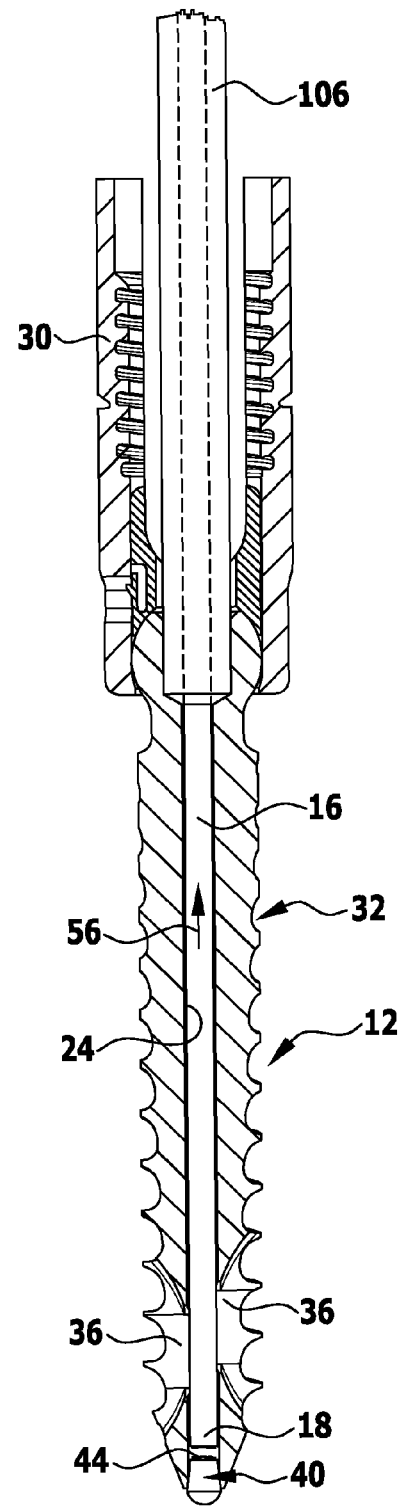

The foregoing summary and the following description may be better understood in conjunction with the drawing figures, of which:

FIG. 1: shows a schematic illustration of a surgical screw system when inserting a bone screw into a bone with the assistance of a K-wire;

FIG. 2A: a schematic, partially sectional view of a distal end of a channeled-out bone screw when pulling out a K-wire with a closure element;

FIG. 2B: a view analogous to FIG. 2A after separating the K-wire from the closure element;

FIG. 3A: a view analogous to FIG. 2A with a further exemplary embodiment of a K-wire;

FIG. 3B: a view of the arrangement depicted in FIG. 3A after the removal of the K-wire from the longitudinal channel of the bone screw;

FIG. 4A: a view analogous to FIG. 2A of a distal end of a bone screw with a conically widening longitudinal channel having an internally threaded section;

FIG. 4B: a view of the arrangement depicted in FIG. 4A with a conical closure element provided with an external thread after the removal of the K-wire;

FIG. 5A: a view similar to FIG. 2A with a further exemplary embodiment of a K-wire;

FIG. 5B: a view of the arrangement depicted in FIG. 5A after the removal of the K-wire from the longitudinal channel of the bone screw;

FIG. 5C: an enlarged, partly sectional view of the region A depicted in FIG. 5A;

FIG. 6A: a view analogous to FIG. 2A with a further exemplary embodiment of a K-wire in the form of a partially sectional illustration;

FIG. 6B: a view of the arrangement depicted in FIG. 6A after separating the K-wire from the closure element;

FIG. 7A: a view analogous to FIG. 2A with a further exemplary embodiment of a K-wire;

FIG. 7B: a sectional view of the arrangement depicted in FIG. 7A in the direction of the arrow B;

FIG. 8A: a view analogous to FIG. 7A with a further exemplary embodiment of a K-wire;

FIG. 8B: a sectional view of the arrangement depicted in FIG. 8A in the direction of the arrow C;

FIG. 9: a schematic illustration of a handle with a jaw chuck for separating the K-wire from the closure element;

FIG. 10A: a schematic illustration of a pulling instrument for removing the K-wire, and in particular for tearing the K-wire away from the closure element; and FIG. 10B: a sectional view of a distal end of the arrangement depicted in FIG. 10A.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical K-wire for guiding a bone screw comprising a longitudinal channel, which said K-wire comprises a proximal and a distal end, wherein a closure element for closing-off the distal end outlet opening of the longitudinal channel of the bone screw is arranged or formed at the distal end.

The proposed configuration of a K-wire makes it possible for the K-wire to be initially introduced into the bone in the conventional manner, by hammering or screwing it in for example, so as to serve as a guide means for the completely channeled-out bone screws. In the next step, the distal end of the bone screw can be pushed over the proximal end of the K-wire and advanced to the bone. In the next step, the bone screw is screwed into the bone. The process of screwing-in the bone screw with the help of the K-wire prevents the lateral cement outlet openings of the bone screw from getting clogged. Finally, the K-wire is pulled out of the screw in the proximal direction, whereby the closure element then closes the bone screw so that bone cement being injected into the proximal end of the bone screw can no longer emerge from the longitudinal channel at the distal end of the bone screw.

It is advantageous, if the closure element is formed such as to be connectable to the K-wire in releasable manner. On the one hand, this simplifies the production of the K-wire since the K-wire and the closure element can be produced independently of one another and only be connected at the end of the production process. On the other hand, this arrangement also makes it possible for the closure element to be released from the K-wire if need be, for example, when removing the K-wire, so that only the closure element remains on the screw at the distal end and thus forms part of the bone screw forming an implant.

The K-wire and the closure element can be separated from one another in a particularly simple manner, if the K-wire comprises a connecting device for connecting the K-wire and the closure element in releasable manner.

It is expedient, if the connecting device is in the form of a force-locking and/or shape-locking connection. In other words, this means that the K-wire and the closure element are connected to each other and/or can be connected to one another in force locking and/or shape locking manner.

The construction of the K-wire is particularly simple, if the connecting device comprises first and second connecting elements which are arranged or formed on the K-wire on the one hand and on the closure element on the other, and which are in mutual engagement in a guidance position in which the K-wire and the closure element are coupled to one another, and are mutually disengaged in a closure position in which the K-wire and the closure element are separated from each other. It is thus possible in particular for the closure element to close a distal end opening of the longitudinal channel of the bone screw in the closure position, i.e. when it is separated from the K-wire. In any case, it is thus possible for the K-wire and the closure element to be separated before or when removing the K-wire from the longitudinal channel of the bone screw after the implantation thereof.

The K-wire and the closure element can be connected to one another in a particularly simple way, if one of the connecting elements is in the form of an internally threaded section and if the other connecting element is in the form of a corresponding externally threaded section. Thus a screw-type connection can be formed in a simple manner in order to screw the K-wire and the closure element together.

Furthermore, it can be advantageous if the first and the second connecting element are in the form of cooperating latching elements which are in mutual engagement in the guidance position and are mutually disengaged in the closure position. Thus, for example, the closure element can be latched to the distal end of the K-wire and can be disengaged therefrom when the K-wire is being withdrawn from the longitudinal channel of the bone screw.

A connecting device in the form of a latching connection can be produced in a particularly simple manner, if one of the latching elements is in the form of a widened portion and if the other latching element is in the form of a hood or cap surrounding the widened portion. Thus, the hood or cap can be pushed onto the distal end and thereby latched onto the widened portion before the K-wire is inserted into the bone. In particular, the widened portion can have a head-like shape so that an undercut is formed, or, it is at least possible for the widened portion to engage behind a part of the hood or cap at the proximal side.

In accordance with a further preferred embodiment of the invention, provision may be made for the K-wire and the closure element to be connected to one another in inseparable manner or to be formed in one piece manner and for a predetermined breaking point to be formed, arranged or provided between the distal end of the K-wire and the closure element. The predetermined breaking point enables the closure element to be separated from the K-wire in a simple manner. For example, it can be torn off or broken off when the K-wire is being pulled out of the longitudinal channel of the bone screw in the proximal direction after the implantation process.

A predetermined breaking point can be formed in a particularly simple manner, if it comprises at least one recess extending in the peripheral direction. It could also be provided in the form of several, two, three or more recesses which extend in the peripheral direction and preferably lie in the same plane.

The recess can be produced in a particularly simple manner, if it is configured to be completely surrounding. In other words, this means that the recess extends through a peripheral angle of 360° on an outer surface of the K-wire in the transition region to the closure element.

Production of the recess is particularly simple, if it is in the form of a notch. For example, a notch can be produced with a notching tool, this thereby leading to re-shaping of the material and thus weakening of the material for the purposes of forming the recess.

Furthermore, it can also be expedient, if the recess is in the form of an annular groove. An annular groove can be produced by a cutting treatment for example.

Preferably, the recess is formed by a cutting treatment and re-shaping process. Dependent on the material used for the production of the K-wire, the one or the other kind of treatment can exhibit advantages.

Expediently, the diameter of the closure element tapers in the proximal direction at least in sections thereof. It may also taper along its entire extent in the longitudinal direction. Such a form of closure element enables an interference-fit or press-fit between the closure element and the distal end of a bone screw to be effected in a simple manner, this being realized when the K-wire is pulled out of the longitudinal channel of the bone screw.

It is expedient, if the closure element has a conical or substantially conical closure section. One such as this can be produced in a simple manner by injection moulding or else by a cutting treatment for example.

It is advantageous, if the connecting element comprised by the closure element is arranged or formed on or in the region of the closure section. Such an arrangement enables a connection between the K-wire and the closure element to be established in a simple manner.

The production of the K-wire can be effected in a particularly simple manner, if the closure element is formed such as to be rotationally symmetrical or substantially rotationally symmetrical.

An interference-fit or force fit between the closure element and a distal end of the bone screw can be optimised in a simple manner when the closure element comprises at least one closure section of non-round cross section which extends in the longitudinal direction. The consequence of this could of course be that the longitudinal channel is not completely closed at the distal end thereof, but leakages developing in this way are so small that emergence of cement is nevertheless very unlikely.

A non-round closure section can be produced in a particularly simple manner, if it has at least one flat portion. For example, a flat portion can be formed by pressing the closure element between two or more clamping jaws. Thus in particular, the flat portion can be produced by deforming or re-shaping the closure element or a distal end of the K-wire.

Furthermore, it can be advantageous if the non-round closure section comprises at least one notch. This too can be produced by a material deforming or re-shaping process. For example, raised structures of this type can be produced by knurling tools. The number of the notches can vary, one, two, three or more notches could be provided. In particular, these may define raised portions of material, particularly widened portions or serrations.

Expediently, the closure section is formed by a material-raising deformation process. A deformation of this type can be produced by simply clamping and applying pressure to the closure section with a pressing tool for example.

Preferably, the K-wire and the closure element are made of different materials. The production of the individual components can be simplified in this way. Furthermore, it is also not necessary for the K-wire to be made of an implantable material since it can be completely removed by pulling it out of the longitudinal channel of the bone screw. This thus makes possible a more economical production process for the K-wire.

A particularly simple and economical manufacturing process for the K-wire can be provided, if it is made of an instrument steel.

Since the closure element is intended to serve for closing-off a distal end of the longitudinal channel of the bone screw on a long term basis, it is advantageous if it is made of a body-compatible implant material. In this way, one can prevent the occurrence of rejection reactions due to the closure element remaining in the body of the patient.

Particularly durable and stable closure of the distal end of the longitudinal channel of the bone screw can be achieved, if the implant material is or contains a metal.

Preferably, the metal is or contains titanium, a titanium alloy, steel, cobalt chrome or a cobalt chromium alloy. The metals mentioned are exceptionally suitable for the production of long-lasting implanatable closure elements.

The production of the K-wire can be further simplified, if the implant material is or contains a synthetic material. In particular, this gives rise to the possibility of manufacturing the closure element from a synthetic material by an injection moulding process.

It is advantageous, if the synthetic material is or contains polyetheretherketone (PEEK), polyethylene (PE), polyethylene having an ultrahigh molecular weight (UHMWPE) or polymethyl methacrylate (PMMA).

Furthermore, the invention also relates to a surgical screw system comprising a bone screw incorporating a longitudinal channel extending from a proximal end up to a distal end and a surgical K-wire for guiding the bone screw, which said K-wire comprises a proximal and a distal end, wherein a closure element for closing-off a distal end outlet opening of the longitudinal channel of the bone screw is arranged or formed at the distal end.

The outlet opening of the longitudinal channel can be closed by the closure element in a simple and secure manner in order to prevent bone cement from emerging through the distal end outlet opening after the removal of the K-wire. The closure element thus enables the advantages of a channeled-out bone screw that is closed at the distal end to be combined with the simultaneous use of a K-wire. The respective disadvantages of using a completely channeled-out screw without a closure element or channeled-out bone screws that are closed at the distal end can thus be overcome.

Preferably, the surgical screw system comprises one of the K-wires described above. The screw system as a whole then also has the advantages mentioned above in connection with the described preferred embodiments of a K-wire.

Advantageously, the bone screw has at least one lateral cement outlet opening. After the implantation of the bone screw, this makes it possible for bone cement to be injected through the longitudinal channel and for a coating of cement to be formed around the shank of the screw commencing from the lateral cement outlet opening. In particular, two, three, four or even more lateral cement outlet openings could also be provided.

It is particularly expedient if the at least one lateral cement outlet opening extends in the radial direction or substantially in the radial direction commencing from the longitudinal channel and if it defines a fluid connection between an outer surface of the bone screw and the longitudinal channel. Such a cement outlet opening permits cement to emerge for the purposes of forming a coating of cement around the shank of the screw in a simple manner.

The production of the screw system can be simplified still further, if the longitudinal channel has a constant or substantially constant internal diameter over the entire length thereof. For example, such a longitudinal channel can be produced by the formation of a boring in the screw body.

In order to enable the channeled-out bone screw to be pushed over a K-wire that has been driven into the bone of the patient, it is expedient if an external diameter of the K-wire is smaller than an internal diameter of the longitudinal channel.

Preferably, a maximum external diameter of the closure element is larger than an internal diameter of the longitudinal channel. In this way, one can prevent in a simple and certain manner, the closure element from being pulled out therewith when the K-wire is being pulled out of the longitudinal channel of the bone screw. Rather, such dimensioning leads to the fact that the closure element will be jammed or wedged in the longitudinal channel of the bone screw in the region of the distal end outlet opening. One can also say that an interference-fit or force fit is formed between the closure element and the bone screws.

In accordance with a further preferred embodiment of the invention, provision may be made for a maximum external diameter of the closure element to be larger than an internal diameter of the longitudinal channel in the region of the distal end thereof or in the region of the distal end opening of the longitudinal channel. This enables the closure element to become jammed or wedged when the K-wire is pulled out of the longitudinal channel of the bone screw so as to close the longitudinal channel in this way.

Furthermore, it can be advantageous if the screw system comprises a coupling device for coupling the closure element to the distal end of the bone screw. The coupling device has the particular advantage that, in dependence on the construction thereof, a defined connection between the closure element and the bone screw can be achieved.

A coupling device in the form of a frictional and/or an interlocking connection is particularly easy to realize. For example, the coupling device can be in the form of a screw-type or bayonet type connection. In particular, the coupling device can thus ensure that the closure element cannot be separated unintentionally from the bone screw and then move freely in the body of the patient in an uncontrolled manner.

The coupling device can be realized in a particularly simple way, if it comprises first and second coupling elements which are arranged or formed on the closure element on the one hand and on the bone screw on the other hand, and which are in mutual engagement in a closed position in which the closure element closes the longitudinal channel of the bone screw at the distal end. A coupling position formed in such a manner can prevent the closure element from being separated from the bone screw in a simple and secure manner.

Preferably one of the coupling elements is in the form of an internally threaded section and the other coupling element is in the form of a corresponding externally threaded section. A screw connection of this type permits a durable secure connection between the closure element and the bone screw. The closure element thus forms a quasi screw-plug for the bone screw.

In order to achieve a durable connection between the closure element and the bone screw that is as secure as possible, it is expedient if the threaded sections are formed such as to be conical or substantially conical. Additionally, due to this design, a jamming process can be achieved in addition to the screw connection of the closure element and the bone screw. Thus a force-locking and shape-locking connection between the closure element and the bone screw is established.

A surgical screw system is schematically illustrated in FIG. 1 and is designated therein by the reference symbol 10. It comprises a bone screw 12 which, in FIG. 1, is exemplarily in the form of a pedicle screw for screwing into a pedicle of a vertebral body of a human spinal column 14. Furthermore, the screw system 10 comprises a K-wire 16 which has a proximal end 100 and a distal end 18.

For the purposes of implanting the bone screw 12, the distal end 18 of the K-wire is firstly driven forwardly into the bone and then, in a next step, a distal end 22 of the bone screw 12 incorporating a longitudinal channel 24 extending from the proximal end 20 up to the distal end 22 thereof is pushed over the proximal end 100 of the K-wire, namely, up to the bone in order to subsequently screw the bone screw 12 further into the bone. The K-wire 16 thus serves for the precise guidance of the bone screw 12 during the implantation thereof. In connection therewith, the external diameter 26 of the K-wire 16 is somewhat smaller than the internal diameter 28 of the longitudinal channel 24.

In principle, the bone screw 12 can be formed in any arbitrary manner. It may, in particular, be a polyaxial screw which comprises a forked screw head 30 that is mounted on the shank in moveable manner and serves for seating not illustrated connecting rods or plates of a spinal column stabilization system. A shank 32 of the bone screw 12 is provided with an external thread 34 which can, in particular, be in the form of a self-tapping thread. Two mutually diametrically opposite lateral cement outlet openings 36, which establish a fluid connection between the longitudinal channel 24 and the surroundings of the shank 32, are formed in the shank 32 somewhat on the proximal side of the distal end 22 thereof. When screwing the bone screw 12 into the bone with the K-wire 16 still in place, both an opening 38 formed at the distal end 22 and the lateral cement outlet openings 36 are substantially blocked by the K-wire 16, this thereby preventing bone material from clogging up the lateral cement outlet openings 36.

In order to prevent the emergence of bone cement when injecting the latter into a proximal end of the longitudinal channel 24 after removing the K-wire 16 as was described in detail hereinabove, a closure element 40 in the form of a plug 42 is formed at the distal end 18 of the K-wire 16. In the case of the exemplary embodiment illustrated schematically in FIG. 2A, the K-wire 16 and the closure element 40 are formed in one piece manner. Between them, there is formed a predetermined breaking point 44 which comprises a recess 46 extending in the peripheral direction. This can alternatively be in the form of a notch 48 or an annular groove 50 formed by a cutting treatment.

A maximum external diameter of the closure element 40 somewhat on the proximal side of a distal end 54 thereof is somewhat larger than the internal diameter 28 of the longitudinal channel 24. If the K-wire 16 is pulled in the direction of the arrow 56 out of the longitudinal channel 24 of the bone screw 12 in the proximal direction after the final placement of the bone screw 12, the closure element 40 is pulled a little into the longitudinal channel 24 and then, due to the selected dimensions, jams in the longitudinal channel 24. The opening 38 is then blocked by the plug 42 in the desired manner. Under further tensile stress, the K-wire 16 finally tears off due to the weakened nature of the predetermined breaking point 44 and can be pulled completely out of the longitudinal channel 24. The plug 42 then remains in the body of the patient as a part of the bone screw 12 forming the implant.

In the exemplary embodiment of a K-wire 16 illustrated in FIG. 3A, the likewise conically shaped closure element 40 is additionally provided with a conical external thread 58. The K-wire 16 and the closure element 40 are likewise formed in one piece manner and are separated from each other by a predetermined breaking point 44 in the form of a notch. When removing the K-wire 16, the plug 42 is screwed into the distal end 22 of the bone screw 12 as the result of a rotary movement. The flanks of the thread of the closure element thereby deform and become jammed in the longitudinal channel 24. At a certain torsional moment, the predetermined breaking point 44 ruptures and the K-wire 16 and the closure element 40 are separated from each other so that the K-wire 16 can be pulled out of the longitudinal channel 24.

Optionally or as an alternative thereto, peripheral grooves or a rough surface could also be used instead of the external thread 58 and could lead to an improvement in the clamping action between the closure element 40 and the longitudinal channel 24 of the bone screw. In arrangements of this type, the closure element is jammed in the longitudinal channel by a tugging movement in the proximal direction. Both the external thread 58 and the grooves described have the advantage that, after the injection of the bone cement, the plug 42 is also held in interlocking manner by the bone cement since the bone cement can still flow around the part of the closure element 40 of tapering diameter during the injection process.

In the case of the bone screw 12 that is schematically illustrated in FIG. 4A, the longitudinal channel 24 widens out somewhat conically in the distal direction in the region between the cement outlet openings 36 and the opening 38. The conically widening section is provided with an internal thread 60. This is formed in a manner corresponding to that of the external thread 58 of the closure element illustrated in FIGS. 3A and 3B. This permits the closure element 40, which is formed in one piece manner with the K-wire 16, to be screwed into the longitudinal channel 44 so that, after the rupture of the predetermined breaking point 44, the plug 42 serving as a kind of closure screw closes the distal end 22 of the longitudinal channel 24, as is schematically illustrated in FIG. 4B. In other words, the external thread 58 forms a first coupling element 112 and the internal thread 60 a second coupling element 114 of a coupling device bearing the general reference symbol 110. The first and the second coupling element are thus arranged or formed on the closure element 40 on the one hand and on the bone screw 12 on the other hand and are in mutual engagement in a closure position in which the closure element 40 closes the longitudinal channel 24 of the bone screw 12 at the distal end.

A further exemplary embodiment of a K-wire 16 with a closure element 40 is schematically illustrated in FIGS. 5A to 5C. In this exemplary embodiment, a connecting device 62 is provided for the purposes of connecting the closure element 40 and the K-wire 16 in releasable manner. It comprises a first connecting element 64 in the form of a head-like widened portion which defines a distal end 18 of the K-wire 16. An annular constriction 68 is formed somewhat on the proximal side of the widened portion 66.

The closure element 40 has a conical closure section 70 and also a substantially hemispherical distal end 54. In the proximal direction, the closure section 70 is provided with a recess 72 corresponding to the widened portion 66 which defines a second connecting element 74 of the connecting device 62 corresponding to the first connecting element 64. The closure element 40 thus forms not just a plug for closing-off the opening 38 but, at the same time, it also forms a hood or cap 76 which surrounds the distal end 54 and its widened portion 66 in snug-fitting manner. Alternatively, the widened portion 66 and the recess 72 could also be in the form of latching elements, in that, as is illustrated schematically in FIG. 5B for example, cuts 78 extending from the proximal end thereof in the longitudinal direction divide the closure section 70 into individual segments which can spring out radially when being pushed or pulled onto the widened portion 66.

When the K-wire 16 is being pulled out, the hood 76 jams in the opening 38 in like manner to the previously described closure elements 40. The widened portion 66 can be wrenched out of the recess 72 by applying a suitable pulling force so that the closure element 40 is separated from the K-wire 16.

A further alternative arrangement of a connecting device 62 is schematically illustrated by the exemplary embodiment of a K-wire 16 that is illustrated in FIGS. 6A and 6B. The closure element 40, the shape of which substantially corresponds to the closure element 40 in the exemplary embodiment illustrated in FIGS. 2A and 2B, comprises a threaded bolt section 80 having a significantly smaller external diameter compared with the internal diameter 28 of the longitudinal channel 24. Starting from the distal end 18, there is provided in the K-wire 16 a blind hole 82 which is open in the distal direction and is provided with an internal thread 84 that is formed in a manner corresponding to an external thread 86 of the threaded bolt section 80. The internal thread 84 and the external thread 86 thus form first and second connecting elements 64, 74 of the connecting device 62. They make it possible, in particular, for the K-wire 16 and the closure element 40 to be made of different materials, for example, from a body-compatible implant material for the closure element 40 on the one hand and from a material that is suitable for the production of a surgical instrument on the other hand although this material does not have to be suitable for long term retention in the body of a patient. A conventional instrument steel comes to mind for this purpose for example.

For the purposes of removing the K-wire, it can either be pulled back so that the threaded bolt tears away from the plug 42 in a manner which is not illustrated in detail whereby the threaded bolt section 80 can be partly pulled out of the longitudinal channel 24 in the proximal direction with the K-wire 16. Another option as schematically illustrated in FIGS. 6A and 6B would be to pull back the K-wire 16 until the closure element 40 jams in the opening 38 and then to unscrew the K-wire 16 from the threaded bolt section 80. In this case, the subsequent injection of the bone cement additionally produces an interlocking connection for the purposes of holding the threaded bolt section 80 and hence the plug 42 in the desired position as is illustrated in FIG. 6B.

A further exemplary embodiment of a K-wire 16 having a closure element 40 that is formed therewith in one piece manner is schematically illustrated in FIGS. 7A and 7B. The closure element 40 in FIG. 7A differs from the closure element of the exemplary embodiment illustrated in FIG. 2A in that the plug 42 has lateral flats or flat portions 88. Consequently, the material, from which the K-wire 16 is produced, is partly raised and thus a conical deformation of the closure element 40 is achieved to at least a partial extent. Such a mode of production makes it possible to form the K-wire 16 and the closure element 40 from a simple piece of wire. This is possible, in particular, using an appropriate flat pressing process with not illustrated pressing jaws. Thus overall an approximately conical shape can be produced from a cylindrical wire material. Since this results in a sealing structure having a cross section that is not completely round, there will of course be no complete closure of the opening 38 of the bone screw 12. The resulting gaps 90 between the longitudinal channel 24 and the plug 42 are, however, very small so that emergence of cement at this point is very unlikely.

Advantageously, a predetermined breaking point 44 between the K-wire 16 and the closure element 40 is likewise produced during the same re-shaping process, for example, by creating one or more notched sections which extend in the peripheral direction. There is no compelling need to have a fully peripherally extending predetermined breaking point 44 in order to produce defined rupture of the K-wire 16 from the closure element 40.

In place of the flat portions 88, notches 92 extending substantially in the longitudinal direction from a distal end 54 of the closure element 40 could also be formed in a cylindrical piece of wire, as is the case in the exemplary embodiment illustrated schematically in FIGS. 8A and 8B. This again results in reshaped and raised portions of material 94 which define a substantially conical outer contour of the closure element 40. Two, three or yet more grooves 92 can be provided, this thereby giving rise to a corresponding number of raised portions of material 94. Such a structure can be created in particular by knurling. When the K-wire 16 is pulled out in the proximal direction, the predetermined breaking point 44 in the exemplary embodiment illustrated in FIGS. 8A and 8B also ruptures so that the closure element 40 jammed in the opening 38 is wedged or stuck with the longitudinal channel in the manner already described above. The plug 42 on the bone screw 12 then remains in the longitudinal channel 24 and prevents bone cement from emerging through the opening 38.

The manner in which the K-wire 16 can be separated from the closure element 40 is schematically illustrated in FIG. 9. A handle 96 with a jaw chuck 98 can be employed for this purpose. The jaw chuck 98 is clamped on and fixed to the proximal end 100 of the K-wire 16. Thereafter, the K-wire 16 is twisted by rotating the handle in the direction of the arrow for example and the predetermined breaking point 44 ruptures. During this process, the bone screw 12 should preferably be held still with the aid of a channeled-out screwdriver for example, although this is not illustrated in FIG. 9. When using such a process, the handle 96 has to be positioned behind the screwdriver.

A surgical instrument in the form of a wire puller 104 is schematically illustrated in FIG. 10A. It likewise comprises clamping jaws which are not illustrated in detail but with which the proximal end of the K-wire can be firmly gripped. The wire puller has a supporting sleeve 106 which projects out at the distal side and can be advanced up to the shank 32 of the screw upon which it is then supported. A movement of the clamping jaws gripping the K-wire 16 in the proximal direction, which is caused by the movement towards one another of two branches 108 that protrude in the proximal direction and are mounted such as to be pivotal relative to each other, enables a pulling force to be applied to the K-wire in order to sever the predetermined breaking point 44.

The basic construction of the wire puller 104 can correspond to the construction of the application instrument described in DE 203 03 657 U1 which together with the entire published content thereof is hereby incorporated in the present application.

The K-wire 16 and the closure element 40 can be formed from the materials that have already been described hereinabove. They can be made of the same or of different materials in dependence on whether they are produced in one piece manner or are produced separately from each other.

The invention claimed is:

1. A surgical screw system comprising:
a bone screw having a longitudinal channel extending from a proximal end up to a distal end, and
a surgical K-wire for guiding the bone screw, the K-wire comprising:
a proximal and a distal end, and
a closure element for closing-off a distal end outlet opening of the longitudinal channel of the bone screw arranged or formed at the distal end,
wherein:
the K-wire and the closure element are connected to one another in an inseparable manner or are formed in a one piece manner and a predetermined breaking point is formed, arranged or provided between the distal end of the K-wire and the closure element,
the closure element comprises at least one closure section extending in a longitudinal direction,
the at least one closure section has a non-round cross section with only two opposing flat surfaces,
the bone screw has at least one lateral cement outlet opening, and
the predetermined breaking point is arranged such that the closure element, after separating from the K-wire at the predetermined breaking point, remains between the distal end outlet opening and the at least one lateral cement outlet opening leaving the at least one lateral cement outlet opening open.

2. A surgical screw system in accordance with claim 1, wherein the closure element is formed such as to be connectable to the K-wire in a releasable manner.

3. A surgical screw system in accordance with claim 1, further comprising a connecting device for connecting the K-wire and the closure element in a releasable manner.

4. A surgical screw system in accordance with claim 3, wherein the connecting device is in a form of at least one of a force-locking connection and a shape-locking connection.

5. A surgical screw system in accordance with claim 3, wherein the connecting device comprises first and second connecting elements which are arranged or formed on the K-wire on the one hand and on the closure element on the other hand and which are in mutual engagement in a guidance position in which the K-wire and the closure element are coupled to one another, and are mutually disengaged in a closure position in which the K-wire and the closure element are separated from each other.

6. A surgical screw system in accordance with claim 5, wherein one of the connecting elements is in a form of an internally threaded section and the other of the connecting elements is in a form of a corresponding externally threaded section.

7. A surgical screw system in accordance with claim 5, wherein the first and the second connecting element comprise cooperating latching elements which are in mutual engagement in the guidance position and are mutually disengaged in the closure position.

8. A surgical screw system in accordance with claim 7, wherein one of the latching elements is in a form of a widened portion and the other of the latching elements is in a form of a hood or cap surrounding the widened portion.

9. A surgical screw system in accordance with claim 5, wherein the connecting element comprised by the closure element is arranged or formed on or in a region of the closure section.

10. A surgical screw system in accordance with claim 1, wherein the predetermined breaking point comprises at least one recess extending in a peripheral direction.

11. A surgical screw system in accordance with claim 10, wherein the at least one recess is in a form of a notch.

12. A surgical screw system in accordance with claim 10, wherein the at least one recess is formed by a cutting treatment or a re-shaping process.

13. A surgical screw system in accordance with claim 1, wherein a diameter of the closure element tapers in a proximal direction at least in sections thereof.

14. A surgical screw system in accordance with claim 1, wherein the closure section is of a substantially conical design.

15. A surgical screw system in accordance with claim 1, wherein the closure element is formed such as to be rotationally symmetrical or substantially rotationally symmetrical.

16. A surgical screw system in accordance with claim 1, wherein the closure section is formed by a material-raising deformation process.

17. A surgical screw system in accordance with claim 1, wherein the K-wire and the closure element are made of different materials.

18. A surgical screw system in accordance with claim 1, wherein a maximum external diameter of the closure element is larger than an internal diameter of the longitudinal channel.

\* \* \* \* \*